US009351709B2

(12) United States Patent
Hague

(10) Patent No.: US 9,351,709 B2
(45) Date of Patent: May 31, 2016

(54) IMAGE PROCESSING METHOD AND APPARATUS AND PROGRAM

(71) Applicant: GE MEDICAL SYSTEMS GLOBAL TECHNOLOGY COMPANY, LLC, Waukesha, WI (US)

(72) Inventor: Hasnine Hague, Tokyo (JP)

(73) Assignee: General Electric Company, Schenectady, NY (US)

( * ) Notice: Subject to any disclaimer, the term of this patent is extended or adjusted under 35 U.S.C. 154(b) by 31 days.

(21) Appl. No.: 14/463,007

(22) Filed: Aug. 19, 2014

(65) Prior Publication Data

US 2015/0055846 A1 Feb. 26, 2015

(30) Foreign Application Priority Data

Aug. 23, 2013 (JP) .................................. 2013-173161

(51) Int. Cl.
  *A61B 8/00* (2006.01)
  *A61B 5/00* (2006.01)
  *G06T 7/00* (2006.01)
  *A61B 8/08* (2006.01)
  *A61B 5/02* (2006.01)
  *A61B 5/055* (2006.01)
  *G01R 33/56* (2006.01)

(52) U.S. Cl.
  CPC ............... *A61B 8/5261* (2013.01); *A61B 5/004* (2013.01); *A61B 5/0035* (2013.01);
  (Continued)

(58) Field of Classification Search
  CPC ... G06T 7/0012; G06T 7/0022; G06T 7/0024; G06T 7/0028; G06T 7/003; G06T 2207/30056; G06T 2207/30101; A61B 5/0035; A61B 5/004; A61B 5/4244; A61B 6/504; A61B 6/52; A61B 6/5211; A61B 8/52; A61B 8/5215
  See application file for complete search history.

(56) References Cited

U.S. PATENT DOCUMENTS 8,111,892 B2   2/2012   Hyun et al. .................... 382/131
8,180,133 B2   5/2012   Omi et al. ...................... 382/131
(Continued)

FOREIGN PATENT DOCUMENTS

| EP | 2131326 B1 | 2/2013 | ............... G06T 7/00 |
| JP | 09-192106 A | 7/1997 | ............... A61B 5/00 |
| JP | 9-192106 A * | 7/1997 | ............... A61B 5/00 |
| JP | 5067398 B2 * | 8/2012 | ............... A61B 8/00 |

OTHER PUBLICATIONS

Olesch et al., Matching CT and Ultrasound data of the Liver by Landmark constrained Image Registration, Proc. of SPIE, dated 2009, pp. 7, vol. 7261, 72610G.
(Continued)

*Primary Examiner* — Andrew W Johns

(57) ABSTRACT

An image processing method for performing registration between a first medical image and a second medical image both being three-dimensional images is provided. The image processing method includes extracting a first vascular image in the first medical image and a second vascular image in the second medical image, detecting at least one vascular portion structure including a plurality of vascular portions close or connected to each other with respect to each of the first and second vascular images extracted, for each of a plurality of combinations of the at least one vascular portion structure in the first vascular image and the at least one vascular portion structure in the second vascular image, performing coordinate transformation on at least one of the first and second vascular images such that a deviation between the vascular portion structures becomes small, and calculating similarity in a prescribed area including the vascular portion structures between the first and second vascular images, and performing coordinate transformation for the registration using the coordinate transformation highest in the calculated similarity.

2 Claims, 10 Drawing Sheets

(52) U.S. Cl.
CPC ............ *A61B 5/7425* (2013.01); *A61B 8/0891* (2013.01); *G06T 7/003* (2013.01); *A61B 5/02007* (2013.01); *A61B 5/055* (2013.01); *A61B 2576/02* (2013.01); *G01R 33/5608* (2013.01); *G06T 2207/10081* (2013.01); *G06T 2207/10088* (2013.01); *G06T 2207/10132* (2013.01); *G06T 2207/10136* (2013.01); *G06T 2207/30056* (2013.01); *G06T 2207/30101* (2013.01)

(56) References Cited

U.S. PATENT DOCUMENTS

2008/0247622 A1* 10/2008 Aylward et al. ............... 382/131
2009/0303252 A1* 12/2009 Hyun et al. .................... 345/643

OTHER PUBLICATIONS

Kirbas et al., A Review of Vessel Extraction Techniques and Algorithms, ACM Computing Surveys, dated Jun. 2004, pp. 81-121, vol. 36, No. 2.

Maes et al., Multimodality Image Registration by Maximization of Mutual Information, IEEE Transactions on Medical Imaging, dated Apr. 1997, pp. 187-198, vol. 16, No. 2.

Lee et al., Building Skeleton Models via 3-D Medial Surface/Axis Thinning Algorithms, CVGIPL Graphical Models and Image Processing, dated 1994, pp. 462-478, vol. 56, No. 6.

English Translation of the JP OA for Application No, 2013-173161. Office Action dated Jan. 19, 2016,.

* cited by examiner

IMAGE PROCESSING METHOD AND APPARATUS AND PROGRAM

CROSS REFERENCE TO RELATED APPLICATIONS

This application claims the benefit of Japanese Patent Application No. 2013-173161 filed Aug. 23, 2013, which is hereby incorporated by reference in its entirety.

BACKGROUND

The present invention relates to a technology for registration between medical images.

As imaging apparatuses, there have heretofore been known, for example, a magnetic resonance apparatus (MR), a radiation tomography imaging apparatus (CT: Computed Tomography), an ultrasound apparatus (US: Ultra Sound), etc. These imaging apparatuses respectively have merits/demerits existing for every imaging modality and may be deficient in diagnosis accuracy only in an image by a specific imaging modality. Therefore, in recent years, attempts have frequently been made to improve diagnosis accuracy by performing a diagnosis using not only the image by the specific imaging modality but also images by a plurality of different imaging modalities.

In the diagnosis using the images by the different imaging modalities, image coordinate systems differ for every imaging modality. Therefore, a technology for correcting positional displacements due to the difference between these coordinate systems and variations/deformation of each organ (i.e., a technology for registration between images) is important.

Meanwhile, as a method of performing registration between a plurality of images different from each other, a method using mutual information is the most common (refer to, for example, IEEE Trans. on Med. Imaging, 16:187-198, 1997). This method is of an intensity based method based on the brightness value of an image in a broad sense. That is, it is a prerequisite that object images have to do with brightness values thereamong to perform registration using the mutual information.

In a US image, however, an acoustic shadow occurs and hence a brightness value at the back of a high reflector is lowered more than the original value. The brightness value of each blood vessel also changes depending on the running direction of the blood vessel. Therefore, for example, in the registration between an MR image and a US image or the registration between a CT image and a US image, the situation in which brightness values have poor relevance often occurs, and there is a case in which the accuracy of registration becomes extremely deteriorated.

With the foregoing in view, there has been a demand for a technology capable of performing registration between medical images with higher accuracy.

BRIEF DESCRIPTION

In a first aspect, an image processing method for performing registration between a first medical image and a second medical image both being three-dimensional images is provided. The method includes an extraction step of extracting a first vascular image in the first medical image and a second vascular image in the second medical image, a detection step of detecting at least one vascular portion structure comprised of a plurality of vascular portions close or connected to each other with respect to each of the first and second vascular images extracted by the extraction step, a computation step of, for each of a plurality of combinations of the vascular portion structure in the first vascular image and the vascular portion structure in the second vascular image, performing coordinate transformation on at least one of the first and second vascular images in such a manner that a deviation between the vascular portion structures becomes small, and calculating similarity in a prescribed area including the vascular portion structures between the first and second vascular images, and a transformation step of performing coordinate transformation for the registration using the coordinate transformation highest in the similarity.

In a second aspect, an image processing apparatus for performing registration between a first medical image and a second medical image both being three-dimensional images is provided. The apparatus includes an extracting unit for extracting a first vascular image in the first medical image and a second vascular image in the second medical image, a detecting unit for detecting at least one vascular portion structure comprised of a plurality of vascular portions close or connected to each other with respect to each of the first and second vascular images extracted by the extracting unit, a computing unit for, for each of a plurality of combinations of the vascular portion structure in the first vascular image and the vascular portion structure in the second vascular image, performing coordinate transformation on at least one of the first and second vascular images in such a manner that a deviation between the vascular portion structures becomes small, and calculating similarity in a prescribed area including the vascular portion structures between the first and second vascular images, and a transforming unit for performing coordinate transformation for the registration using the coordinate transformation highest in the similarity.

In a third aspect, the image processing apparatus according to the second aspect is provided, wherein the plurality of combinations are combinations of a plurality of vascular portion structures in the first vascular image, and a plurality of vascular portion structures in the second vascular image.

In a fourth aspect, the image processing apparatus according to the second aspect, wherein the plurality of combinations are combinations of a single vascular portion structure in the first vascular image selected, and a plurality of vascular portion structures in the second vascular image.

In a fifth aspect, the image processing apparatus according to any one of the second to fourth aspects is provided, wherein the vascular portion structure includes vascular bifurcation points and two vascular portions branched from each of the vascular bifurcation points.

In a sixth aspect, the image processing apparatus according to the fifth aspect is provided, wherein the computing unit performs the coordinate transformation in such a manner that the vascular bifurcation points are overlaid on each other and planes including two straight lines approximated to the two vascular portions are overlaid on each other.

In a seventh aspect, the image processing apparatus according to any one of the second to fourth aspects is provided, wherein the vascular portion structure includes a first vascular bifurcation point, a single first vascular portion extending from the first vascular bifurcation point, a second vascular bifurcation point different from the first vascular bifurcation point, and a single second vascular portion extending from the second vascular bifurcation point.

In an eighth aspect, the image processing apparatus according to the seventh aspect is provided, wherein the computing unit performs the coordinate transformation in such a manner that prescribed points each being the first vascular bifurcation point, the second vascular bifurcation point or a middle point of a line segment connecting two straight lines approximated to the first vascular portion and the second vascular portion at the shortest distance are overlaid on each other, and planes defined by the two straight lines are overlaid on each other.

In a ninth aspect, the image processing apparatus according to any one of the second to fourth aspects is provided, wherein the vascular portion structure includes two vascular portions different from vascular portions that configure vascular bifurcations.

In a tenth aspect, the image processing apparatus according to the ninth aspect is provided, wherein the computing unit performs the coordinate transformation in such a manner that middle points of line segments each connecting two straight lines approximated to the two vascular portions at the shortest distance are overlaid on each other, and planes defined by the two straight lines are overlaid on each other.

In an eleventh aspect, the image processing apparatus according to any one of the second to tenth aspects is provided, further including adjusting unit for performing coordinate transformation of at least one of the first and second medical images, based on a feature amount related to a pixel value in each of the first and second medical images subjected to the coordinate transformation to thereby perform an adjustment to the registration.

In a twelfth aspect, the image processing apparatus according to any one of the second to eleventh aspects is provided, further including a generating unit for generating a corresponding sectional image at each of the first and second medical images to each of which the registration adjustment is made, and an output unit for outputting the corresponding sectional image at each of the first and second medical images.

In a thirteenth aspect, the image processing apparatus according to any one of the second to twelfth aspects is provided, wherein the detecting unit detects the vascular portion structure by tracking from the thickest vascular portion side in each of the first and second vascular images.

In a fourteenth aspect, the image processing apparatus according to any one of the second to thirteenth aspects is provided, wherein the first and second medical images are images different from each other in imaging modality.

In a fifteenth aspect, the image processing apparatus according to the fourteenth aspect is provided, wherein one of the first and second medical images is an image by an ultrasonic diagnostic apparatus.

In a sixteenth aspect, the image processing apparatus according to any one of the second to fifteenth aspects is provided, wherein the first and second medical images are respectively an image including a liver.

In a seventeenth aspect, the image processing apparatus according to the sixteenth aspect is provided, wherein the first and second vascular images are images each corresponding to a portal vein or a hepatic vein.

In an eighteenth aspect, the image processing apparatus according to any one of the second to seventeenth aspects is provided, wherein the extracting unit extracts the first and second vascular images as binarized images.

In a nineteenth aspect, the image processing apparatus according to any one of the second to eighteenth aspects is provided, wherein the detecting unit detects the vascular portion structure after thinning of the plurality of vascular portions.

In a twentieth aspect, a program for causing a computer to function as an image processing apparatus according to any one of the second to nineteenth aspects is provided.

According to the above aspects, with the above configuration, coordinate transformation is performed such that some vascular structures are most matched, by using the fact that vascular structures corresponding to each other are substantially the same between images representing the same subject. Therefore, even when relevance of brightness values is low between images targeted for registration, registration can be performed without being affected by it, thus resulting in enabling higher-accuracy registration to be performed.

DETAILED DESCRIPTION

Exemplary embodiments will hereinafter be described. Incidentally, the disclosure is not limited to or by the specific embodiments described herein.

First Embodiment

Figure 1:
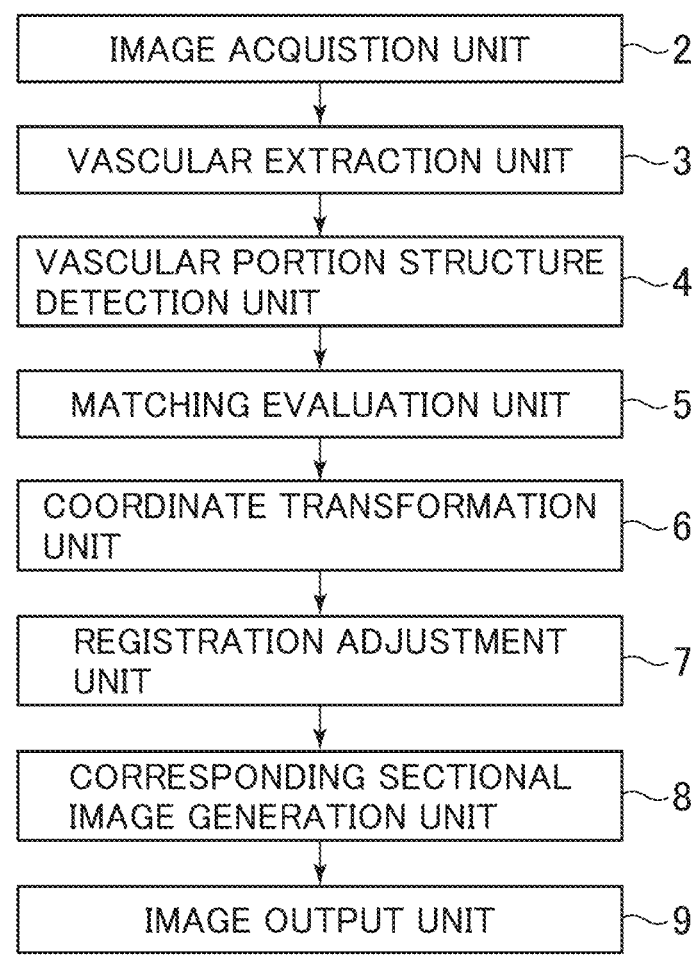
FIG. 1 is a functional block diagram schematically showing a configuration of an image processing apparatus 1 according to a first embodiment.

FIG. 1 is a functional block diagram schematically showing the configuration of the image processing apparatus 1 according to the first embodiment. Incidentally, the image processing apparatus 1 can be implemented by, for example, causing a computer to execute a predetermined program.

As shown in FIG. 1, the image processing apparatus 1 has an image acquisition unit 2, a vascular extraction unit 3, a vascular portion structure detection unit 4, a matching evaluation unit 5, a coordinate transformation unit 6, a registration adjustment unit 7, a corresponding sectional image generation unit 8, and an image output unit 9. Incidentally, the vascular extraction unit 3, the vascular portion structure detection unit 4, the matching evaluation unit 5, the coordinate transformation unit 6, the registration adjustment unit 7, the corresponding sectional image generation unit 8, and the image output unit 9 are respectively examples of extracting unit, detecting unit, evaluating unit, transforming unit, adjusting unit, generating unit and output unit.

Figure 2:
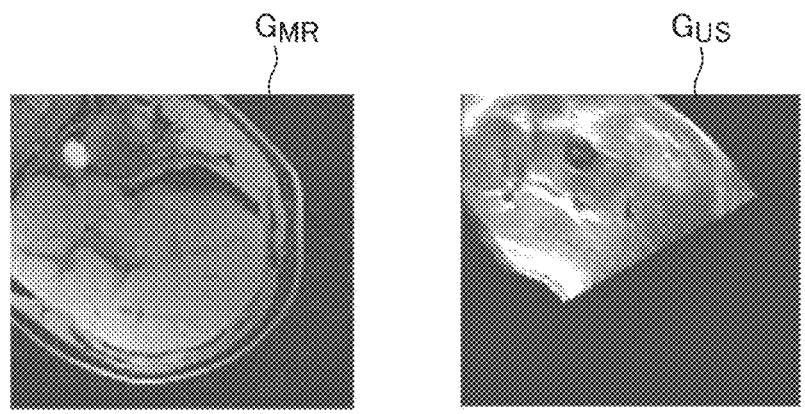
FIG. 2 is a diagram illustrating one example of an MR image GMR and a US image GUS representing the liver of the same subject.

The image acquisition unit 2 acquires two images targeted for registration. The image acquisition unit 2 normally acquires two input three-dimensional medical images as two images targeted for registration according to the operation of a user. The image acquisition unit 2 sets one of the two images to a target image fixed in registration processing and sets the other thereof to an object image to be coordinate-transformed in the registration processing. In the first embodiment, the image acquisition unit 2 acquires an MR image GMR and a US image GUS representing the liver of the same subject as the two three-dimensional medical images targeted for the registration. Further, the image acquisition unit 2 sets the US image GUS to a target image and sets the MR image GMR to an object image. Incidentally, the MR image GMR and the US image GUS are examples of a first medical image and a second medical image. FIG. 2 shows an example illustrative of an MR image GMR and a US image GUS representing the liver of the same subject. In the figure, however, a prescribed sectional image in a three-dimensional medical image is shown for convenience.

Figure 3A:
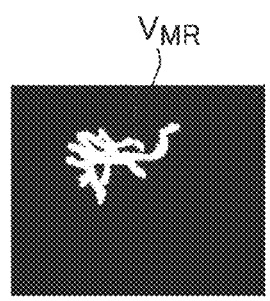
FIGS. 3A-3C are diagrams showing each example of calculation results of vectors U, V and W at an MR vascular image VMR, an MR vascular tree bone TRMR and an MR vascular bifurcation.

The vascular extraction unit 3 extracts vascular images representing blood vessels with respect to the MR image GMR and the US image GUS. A known method is used for the extraction of the vascular images. A method is used which has been described in, for example, Kirbus C and Quek, F: A review of vessel extraction technique and algorithms, ACM Computer Surveys (CSUR), 36 (2), 81-121, 2004. Hereinafter, the vascular image in the MR image GMR is referred to as an MR vascular image VMR, and the vascular image in the US image GUS is referred to as a US vascular image VUS. In the first embodiment, an image representing portal vein or hepatic vein of the liver is extracted as a vascular image. Further, the vascular image is extracted as a binarized image. Incidentally, the MR vascular image VMR and the US vascular image VUS are examples of a first vascular image and a second vascular image. FIG. 3A shows a sample of an MR vascular image VMR as an example of a vascular image.

The vascular portion structure detection unit 4 detects one or more vascular portion structures from the extracted MR vascular image VMR and US vascular image VUS. The vascular portion structure is a structure configured by a plurality of vascular portions close to each other or connected to each other. In the first embodiment, a vascular bifurcation is detected as the vascular portion structure. The vascular bifurcation is composed of a vascular bifurcation point and two vascular portions branched from the vascular bifurcation point. Therefore, the vascular bifurcation is specified and identified by the position of the vascular bifurcation point and the running directions and lengths of the two vascular portions branched from the vascular bifurcation point. The vascular portion structure detection unit 4 specifically performs the following processing.

First, the vascular portion structure detection unit 4 performs smoothing processing on the extracted MR vascular image VMR and US vascular image VUS. It is thus possible to obtain a vascular image of which the boundary (contour) is made smooth. For example, a three-dimensional Gaussian Filter, a three-dimensional Median Filter or the like is used for the smoothing processing.

Figure 3B:
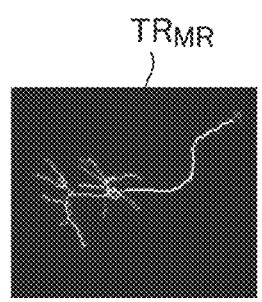

Next, the vascular portion structure detection unit 4 performs skeleton processing (three-dimensional thinning processing) on the smoothing-processed MR vascular image VMR and US vascular image VUS. It is thus possible to obtain "vascular tree bones" in which only axes of blood vessels along their running directions are represented in linear form like tree bifurcation bones. Hereinafter, the vascular tree bone obtained from the MR vascular image is called an MR vascular tree bone TRMR, and the vascular tree bone obtained from the US vascular image is called a US vascular tree bone TRUS. As the skeleton processing, there is used a method described in, for example, Lee et. al, Building skeleton models via 3-D medial surface/axis thinning algorithms, Computer Vision, Graphics, and Image Processing, 56 (6): 462-478, 1994. A sample of the MR vascular tree bone TRMR is shown in FIG. 3B as one example of a vascular tree bone. In FIG. 3B, a number assigned to each vascular portion is a tag number.

Figure 4:
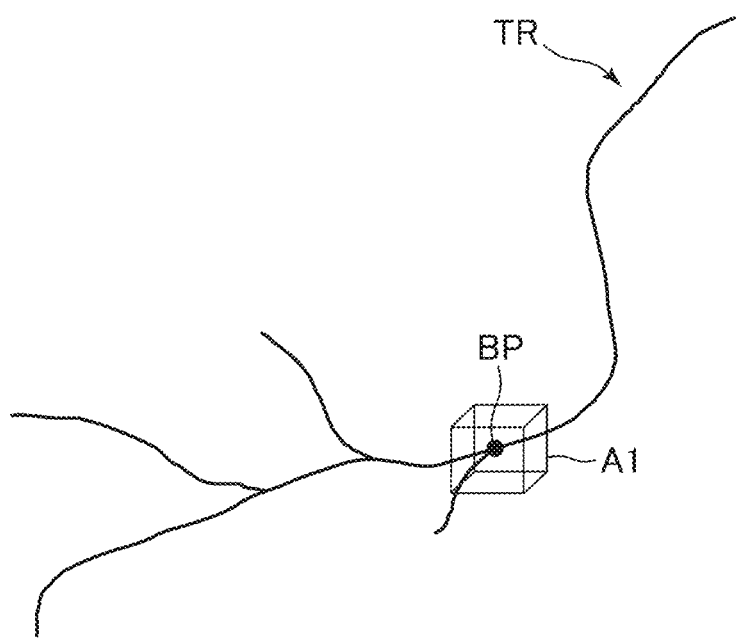
FIG. 4 is a diagram for describing a method of detecting a vascular bifurcation point.

Next, the vascular portion structure detection unit 4 detects one or more vascular bifurcation points at the MR vascular tree bone TRMR and the US vascular tree bone TRUS. Specifically, as shown in FIG. 4, the vascular portion structure detection unit 4 sets as an analysis area A1, an area of a prescribed size, including points on bifurcation bones of a vascular tree bone TR, along the bifurcation bones thereof. The analysis area A1 is taken as a three-dimensional area of [3×3×3] pixels centering on pixels corresponding to the points on the bifurcation bones of the vascular tree bone TR, for example. Next, the vascular portion structure detection unit 4 performs an analysis on the analysis area A1 to detect continuous pixels that form vascular bifurcations. As to the analysis, it is started from the end of a bifurcation bone equivalent to the thickest vascular portion in the vascular image used as the base of the vascular tree bone in such a manner as to be performed from the "trunk" side of the vascular tree bone to the "bifurcation tip" side. Then, the point where the continuous pixels are branched is detected as a vascular bifurcation point BP. Incidentally, although a two-way bifurcation for causing one blood vessel to branch into two blood vessels is general as the vascular bifurcation, three or more-way bifurcation for causing one blood vessel to branch into three or more blood vessels also exist. The three or more-way bifurcations are recognized as a plurality of two-way bifurcations. Hereinafter, each of vascular bifurcation points detected in the MR vascular tree bone TRMR is referred to as an MR vascular bifurcation point $BPMR,i$ (where i=1, 2, . . . ), and each of vascular bifurcation points detected in the US vascular tree bone TRUS is referred to as a US vascular bifurcation point $BPUS,j$ (where j=1, 2, . . . ).

Incidentally, when the vascular bifurcation points are detected, for the sake of simplification, in the whole vascular tree bone, vascular bifurcation points at which the lengths of vascular portions branched from the vascular bifurcation point are very small are eliminated, and only vascular bifurcation points at which the lengths of branched vascular portions are relatively large beyond a predetermined threshold may be detected.

Next, two vectors corresponding to two vascular portions branched from each of the MR vascular bifurcation point $BPMR,i$ and US vascular bifurcation point $BPUS,j$ are determined. Specifically, the following processing is performed.

Figure 5A:
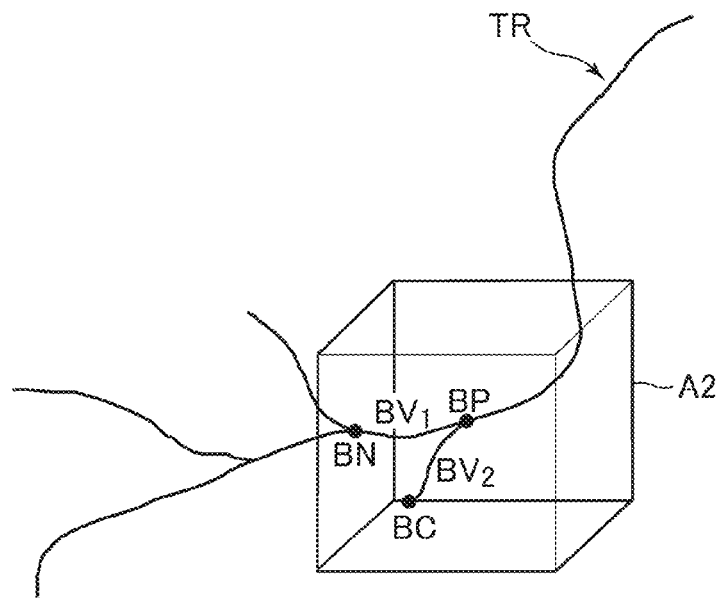
FIGS. 5A and 5B are diagrams for describing a method of determining vectors corresponding to vascular portions that form vascular bifurcations.
Figure 5B:
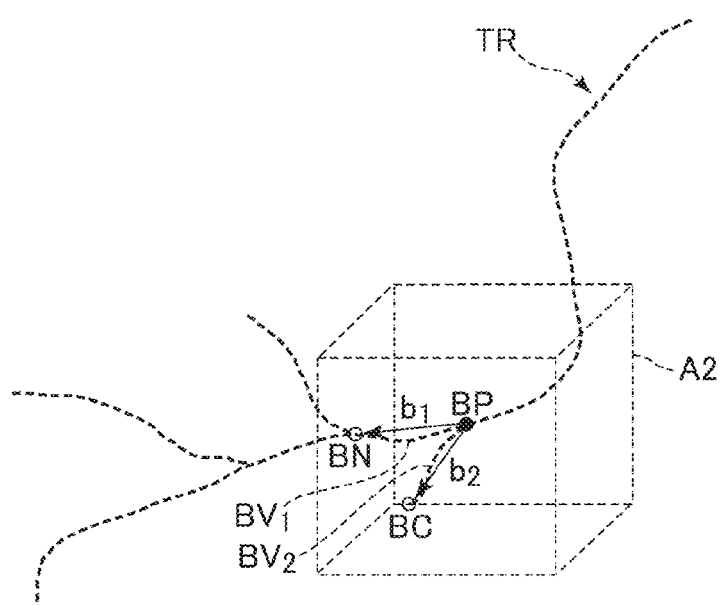

As shown in FIG. 5A, an area of a predetermined size including a vascular bifurcation point BP is set as an attention area A2 for each vascular bifurcation point BP on the vascular tree bone TR. The attention area A2 is taken as a three-dimensional area of [10×10×10] pixels (voxels) centering on the vascular bifurcation point BP, for example. Two vascular portions BV1 and BV2 that branch off from the vascular bifurcation point BP are included in the attention area A2. Next, as shown in FIG. 5B, vectors b1 and b2 indicating the running directions and lengths of the two vascular portions BV1 and BV2 are determined. The running direction and length of one of the vascular portions BV1 and BV2 branched from the vascular bifurcation point BP are assumed to be the direction and length of a line segment that connects the targeted vascular bifurcation point BP and its subsequent vascular bifurcation point BN where the next vascular bifurcation point BN appears in the vascular portion branched from the vascular bifurcation point BP within the attention area A2. On the other hand, when a specific point BC that is an end point or a point of intersection with the boundary face of the attention area A2 appears in the vascular portion branched from the targeted vascular bifurcation point BP, the running direction and length of the other thereof are assumed to be the direction and length of a line segment that connects the targeted vascular bifurcation point BP and the specific point BC.

By such processing, the vascular bifurcation can be identified by the coordinates of the pixels corresponding to the vascular bifurcation point and the two vectors corresponding to the two vascular portions branched from the vascular bifurcation point at each of the MR vascular tree bone TRMR and the US vascular tree bone TRUS. Incidentally, hereinafter, the vascular bifurcation at the MR vascular tree bone TRMR is referred to as an MR vascular bifurcation, and the vascular bifurcation at the US vascular tree bone TRUS is referred to as a US vascular bifurcation.

The matching evaluation unit 5 performs a matching evaluation between the vascular bifurcations for every combination of the MR vascular bifurcation and the US vascular bifurcation. In the first embodiment, the smoothing-processed MR vascular image VMR and US vascular image VUS are in registration with each other in such a manner that the MR vascular bifurcation and the US vascular bifurcation targeted for the matching evaluation are overlaid on each other. Next, the matching evaluation unit 5 calculates similarity around the MR vascular bifurcation and US vascular bifurcation targeted for the matching evaluation, between the registered MR vascular image VMR and US vascular image VUS. The larger the value of similarity, the more the vascular bifurcations are evaluated to be more matched. Specifically, the following processing is performed for every combination of the MR vascular bifurcation and US vascular bifurcation targeted for the matching evaluation.

Figure 6:
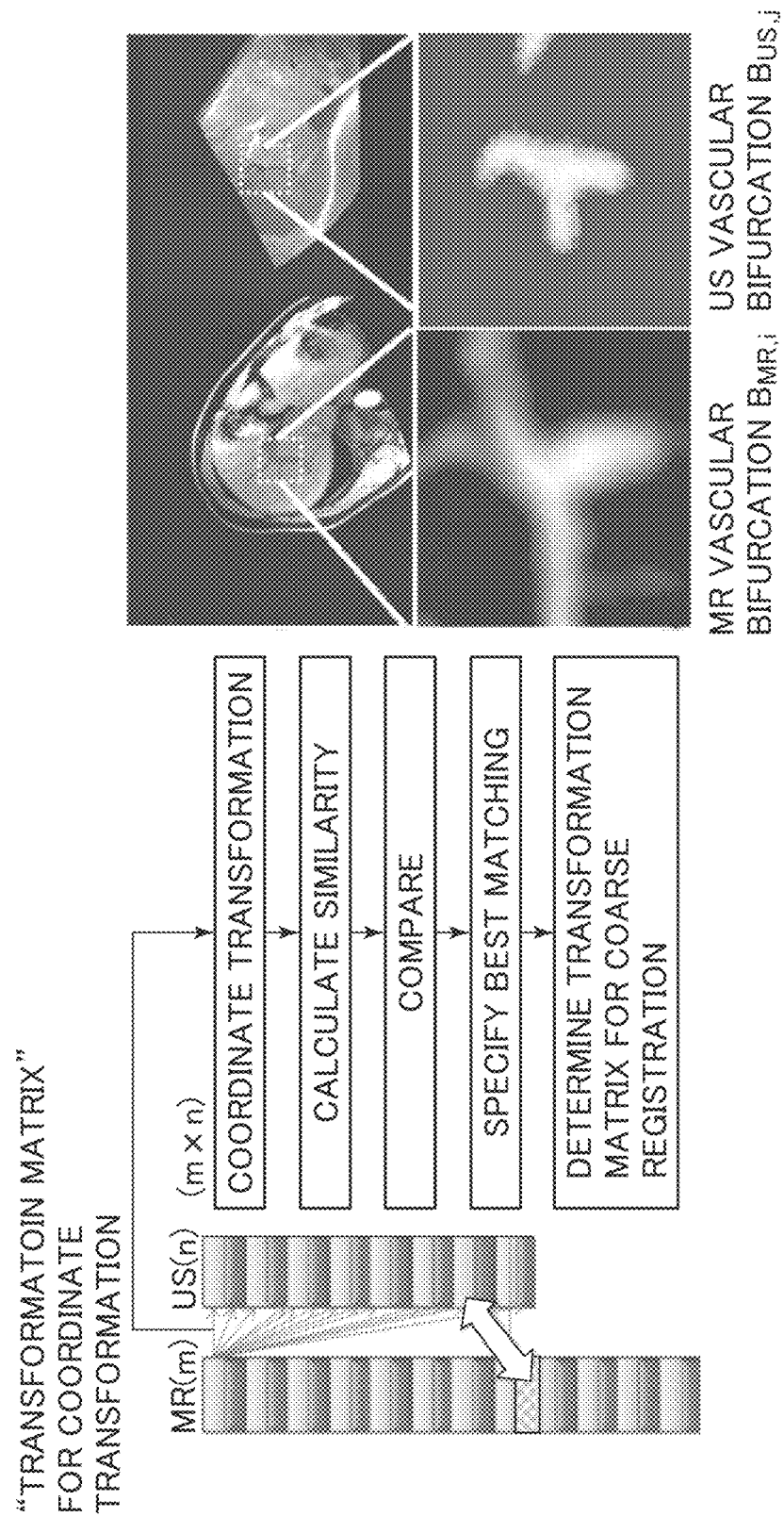
FIG. 6 is a conceptual diagram of a matching evaluation of each vascular bifurcation.

A conceptual diagram of a matching evaluation for each vascular bifurvation is shown in FIG. 6. The matching evaluation unit 5 first performs coordinate conversion on the smoothing-processed MR vascular image VMR and US vascular image VUS and places these vascular images in a coordinates space common to the MR vascular bifurcation and US vascular bifurcation targeted for the matching evaluation.

This coordinates space is a coordinates space defined in such a manner that the MR vascular bifurcation point of the MR vascular bifurcation targeted for the matching evaluation and the US vascular bifurcation point of the US vascular bifurcation targeted for the matching evaluation are overlaid on each other, and further a plane including two vectors corresponding to two vascular portions that form the MR vascular bifurcations, and a plane including two vectors corresponding to two vascular portions that form the US vascular bifurcations are overlaid on each other. This coordinates space is hereinafter called a first common coordinates space. In order to place the smoothing-processed MR vascular image VMR in the first common coordinates space, a transformation matrix corresponding to the MR vascular bifurcation targeted for the matching evaluation is determined, and the coordinate transformation of the MR vascular image VMR is performed using the transformation matrix. Likewise, in order to place the smoothing-processed US vascular image VUS in the first common coordinates space, a transformation matrix corresponding to the US vascular bifurvation targeted for the matching evaluation is determined, and the coordinate transformation of the US vascular image VUS is performed using the transformation matrix.

Figure 3C:
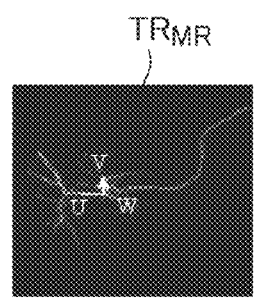
Figure 7:
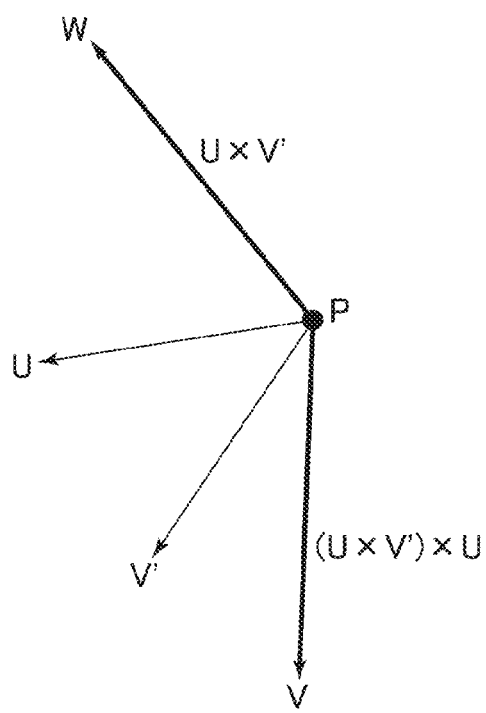
FIG. 7 is a diagram for describing vectors that define vascular bifurcations.

A description will be made of how to determine the transformation matrix. The transformation matrix is comprised of a point of origin to be taken as the center of the first common coordinates space, and a rotation matrix that defines the posture (orientation) of each vascular bifurcation. As shown in FIG. 7, a vascular bifurcation point is taken to be P=[px, py, pz], vectors corresponding to vascular portions branched from the vascular bifurcation point P are taken to be U and V', and a vector orthogonal to a UV plane, (i.e., a normal vector) is taken to be W. Further, a vector orthogonal to a WU plane is taken to be V. Then, the vectors U, V and W orthogonal to each other are determined according to the posture of the vascular bifurcation and define the rotation matrix. A sample of a calculation result of the vectors U, V and W at the MR vascular bifurcation is shown in FIG. 3C.

$$U=[u_x,u_y,u_z], V'=[v'_x,v'_y,v'_z]$$

$$W=U \times V'=[w_x,w_y,w_z]$$

$$V=(U \times V') \times U=[v_x,v_y,v_z]$$

The translation matrix is determined with respect to each of the MR vascular bifurcation detected at the MR vascular tree bone TRMR and the US vascular bifurcation detected at the US vascular tree bone TRUS. The translation matrix TMR-BF determined for the MR vascular bifurcation, and the translation matrix TUS-BF determined for the US vascular bifurcation can respectively be represented as follows:

$$T_{MR\text{-}BF} = \begin{bmatrix} u_x & u_y & u_z & p_x \\ v_x & v_y & v_z & p_y \\ w_x & w_y & w_z & p_z \\ 0 & 0 & 0 & 1 \end{bmatrix}_{MR} \quad \text{Equation 1}$$

$$T_{US\text{-}BF} = \begin{bmatrix} u_x & u_y & u_z & p_x \\ v_x & v_y & v_z & p_y \\ w_x & w_y & w_z & p_z \\ 0 & 0 & 0 & 1 \end{bmatrix}_{US}$$

Incidentally, when there is a difference in scale between the MR image GMR and the US image GUS, the difference in scale can be canceled by multiplying the translation matrix corresponding to the MR vascular bifurcation or the US vascular bifurcation by a scale ratio scal. A matrix of the scale ratio between the MR image GMR and the US image GUS can be represented as follows:

$$scal = \begin{bmatrix} f_x & 0 & 0 & 0 \\ 0 & f_y & v_z & 0 \\ 0 & 0 & f_z & 0 \\ 0 & 0 & 0 & 1 \end{bmatrix} \quad \text{Equation 2}$$

where scale parameters fx, fy and fz are determined from the scale ratio in a corresponding real space between the MR image GMR and the US image GUS.

The matching evaluation unit 5 calculates similarity between the MR vascular image VMR and the US vascular image VUS after the smoothing-processed MR vascular image VMR and US vascular image VUS are placed in the first common coordinates space. Specifically, in the first common coordinates space, the matching evaluation unit 5 sets an area of a predetermined size including the point of origin of the first common coordinates space as an evaluation area with respect to each of the MR vascular image VMR and the US vascular image VUS. The evaluation area is taken to be, for example, a three-dimensional area of [64×64×64] pixels(voxels) centering on its point of origin. Then, the matching evaluation unit 5 calculates similarity in the evaluation area between the MR vascular image VMR and the US vascular image VUS. For example, a mutual correlation coefficient is used as the similarity. A correlation function used in the calculation of the mutual correlation coefficient may be a known one.

The coordinate transformation of the MR vascular image and US vascular image to the first common coordinates space, and the calculation of the similarity such as described above are respectively performed for every combination of the MR and US vascular bifurcations. That is, assuming that the number of MR vascular bifurcations is m and the number of US vascular bifurcations is n, a transformation matrix of the m MR vascular bifurcations and a transformation matrix of the n US vascular bifurcations can be represented as follows:

{T1MR-BF, T2MR-BF, . . . , TmMR-BF} {T1US-BF, T2US-BF, . . . , TnUS-BF} Then, the above-described matching evaluation processing is performed by the number of combinations of the MR and US vascular bifurcations, i.e., the number of m×n. However, whether or not there is a possibility that the vascular portion of any of the MR vascular bifurcations and the vascular portion of any of the US vascular bifurcations will be the common same blood vessel is unknown unless the matching evaluation is performed. Therefore, actually, the matching evaluation is required to be performed on either the MR vascular bifurcation or the US vascular bifurcation for every combination of the MR and US vascular bifurcations even where one of the two vascular portions that form the vascular bifurcations and the other thereof are positionally replaced with each other. Thus, strictly, the above matching evaluation processing is performed by the number of m×n×2.

The matching evaluation unit 5 further compares calculated similarities and specifies the combination of vascular bifurcations related to the best matching (i.e., the combination of vascular bifurcations maximum in similarity) as one representing the same vascular bifurcation common to the MR and US images. Then, the matching evaluation unit 5 determines a transformation matrix used for the coordinate transformation of the MR image on the basis of a transformation matrix corresponding to the combination.

A transformation matrix suitable for coarse registration is obtained from the following equation:

TMR-US=[TMR-BF]best[TUS-BF]$^{-1}$best[scal]

where [TMR-BF]best is a transformation matrix corresponding to MR vascular bifurcations brought to the best matching, and [TUS-BF]$^{-1}$best is an inverse matrix of a transformation matrix corresponding to US vascular bifurcations brought to the best matching.

The coordinate transformation unit 6 performs coordinate transformation of an MR image GMR using the optimal transformation matrix TMR-US to thereby coarsely register the MR image GMR with the US image GUS.

The registration adjustment unit 7 performs fine registration on the coarsely-registered MR image GMR and US image GUS. As for the fine registration, there are used a method for performing coordinate transformation in such a manner that characteristic portions such as pixels values, concentration gradients, edges or the like between images to be registered match with each other, etc.

As one method suitable for the fine registration in the first embodiment, may be mentioned, a method using a Normalized Gradient Field (NGF) (e.g., a method described in Proceeding of SPIE Vol. 7261, 72610G-1, 2009). The normalized gradient field is that a primary partial differential in each of x, y and z directions (i.e., a Gradient Vector is calculated at coordinates on an image, and thereafter the Gradient Vector is normalized by its length (Vector Norm)). That is, the normalized gradient field is a feature amount which does not depend on the magnitude of a pixel value or a brightness value and the magnitude of a gradient and indicates only a gradient direction. If the normalized gradient field of the same direction is generated in positions corresponding to each other at given two images, these two images can be taken to be matched each other in position. Thus, in this method, it is possible to perform registration by optimizing the degree of matching of the directions indicated by the normalized gradient field.

The corresponding sectional image generation unit 8 generates sectional images corresponding to each other at the registered MR image GMR and US image GUS. The sectional position of each of the generated sectional images is designated by an operator.

Figure 8:
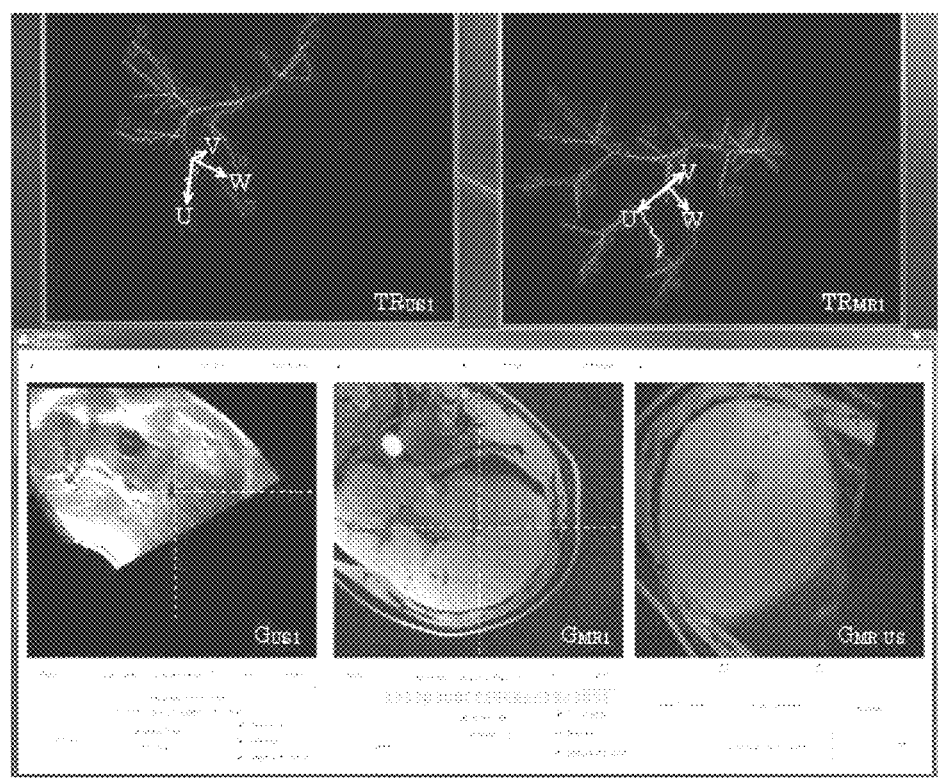
FIG. 8 is a diagram showing one example of an image display.

The image output unit 9 displays the generated sectional images on its screen and outputs the same to the outside as image data. At this time, the combinations of the vascular bifurcations placed in the best matching may be imaged and outputted together. For example, the image output unit 9 displays, for example, the MR vascular tree bone TRMR and the US vascular bone tree TRUS side by side and displays the vascular bifurcation points configuring the vascular bifurcations subjected to the best matching and the vectors of the vascular portions forming the vascular bifurcations on these images emphatically by coloring or the like. One example of an image display is shown in FIG. 8. In FIG. 8, an upper-stage left image is a US vascular tree bone TRMR1 including a result displayed by determining vectors U, V and W corresponding to US vascular bifurcations, and an upper-stage right image is an MR vascular tree bone TRUS1 including a result displayed by determining vectors U, V and W corresponding to MR vascular bifurcations. Further, a lower-stage left image is a predetermined sectional image GUS1 of a coordinate-transformed US image including a specified US vascular bifurcation brought to the best matching, and a lower-stage central image is a predetermined sectional image of a coordinate-transformed MR image GMR1 including a specified MR vascular bifurcation brought to the best matching. A lower-stage right image is an arbitrary sectional image GMR-US of an MR image coarsely registered with an US image G.

Figure 9:
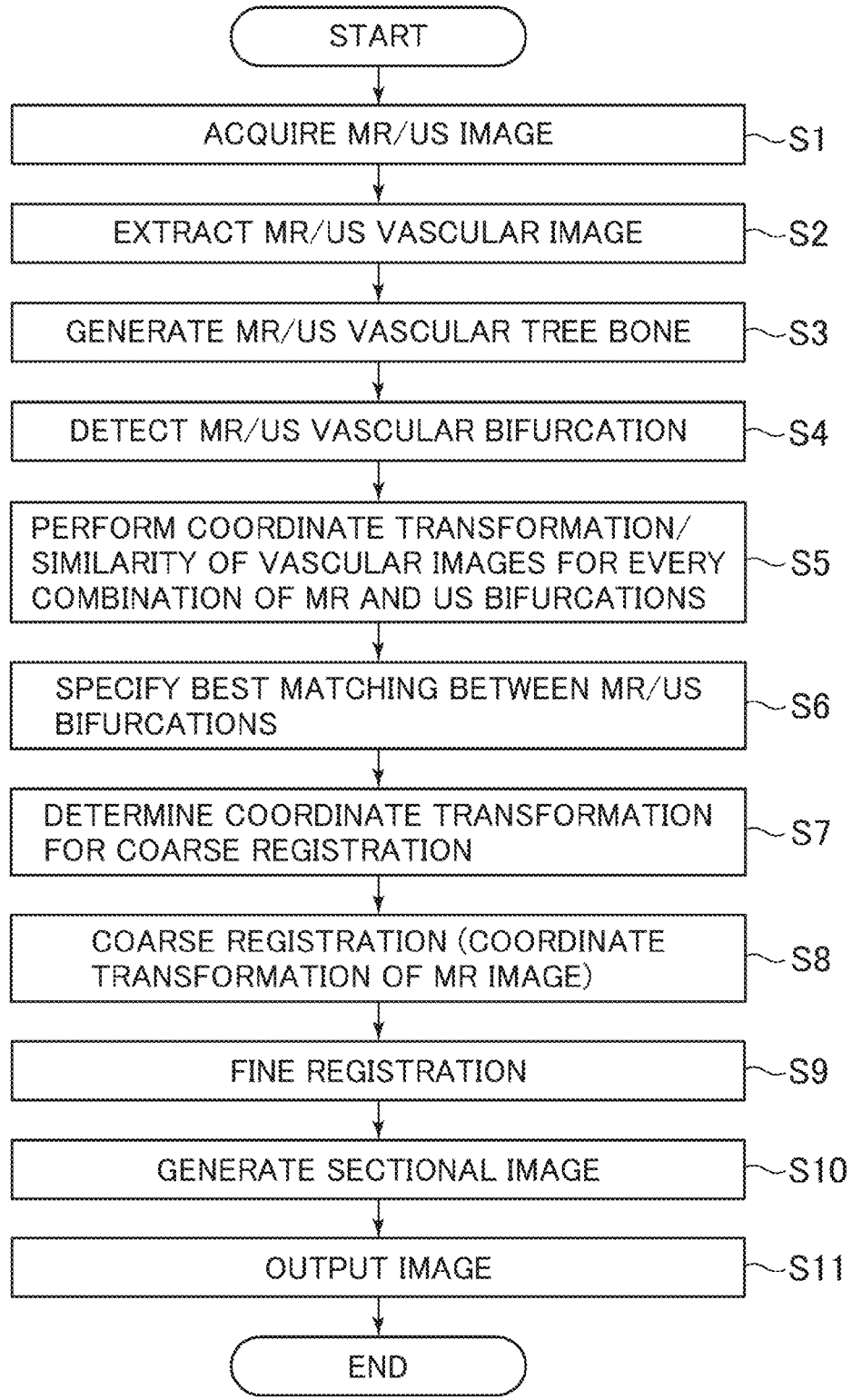
FIG. 9 is a flow diagram showing the flow of processing in the image processing apparatus 1 according to the first embodiment.

The flow of processing by the image processing apparatus 1 according to the first embodiment will be described as follows. FIG. 9 is a flow diagram showing the flow of the processing by the image processing apparatus 1 according to the first embodiment.

At step S1, the image acquisition unit 2 acquires an MR image GMR and a US image GUS of the liver of the same subject. In the first embodiment, the US image $G_{US}$ is assumed to be a target image, and the MR image GMR is assumed to be a target image.

At step S2, the vascular extraction unit 3 extracts a vascular image representing a blood vessel equivalent to the portal vein or hepatic vein of the liver with respect to each of the MR image GMR and the US image GUS. The known method is used for its extraction. The vascular image is extracted as a binarized image.

At step S3, the vascular portion structure detection unit 4 performs smoothing processing and skeleton procession on each of an MR vascular image VMR extracted from the MR image GMR and a US vascular image VUS extracted from the US image GUS to obtain an MR vascular tree bone TRMR and a US vascular tree bone TRUS.

At step S4, the vascular portion structure detection unit 4 performs an analysis on each of the MR vascular tree bone TRMR and the US vascular tree bone TRUS while tracking along the tree bone. With this analysis, one or more vascular bifurcations are detected by determining the position of a vascular bifurcation point and vectors corresponding to two vascular portions branched from the vascular bifurcation point.

At step S5, the matching evaluation unit 5 registers the smoothing-processed MR vascular image VMR and the smoothing-processed US vascular image VUS with each other for every combination of the MR and US vascular bifurcations targeted for the matching evaluation in such a manner that the vascular bifurcations are overlaid on each other. Then, the matching evaluation unit 5 calculates similarity around the targeted MR and US vascular bifurcations between the registered MR vascular image VMR and US vascular image VUS.

At step S6, the matching evaluation unit 5 specifies the combination of vascular bifurcations in which the maximum similarity is calculated, as the combination of vascular bifurcations brought to the best matching.

At step S7, the matching evaluation unit 5 determines a transformation matrix TMR-US used in the coordinate transformation of images for coarse registration on the basis of the transformation matrix corresponding to the vascular bifurcations brought to the best matching.

At step S8, the coordinate transformation unit 6 coarsely registers the MR image GMR with the US image GUS by performing coordinate transformation using the transformation matrix TMR-US determined at step S7.

At step S9, the registration adjustment unit 7 performs fine registration on the coarsely-registered MR image GMR and US image GUS to carry out a registration adjustment. As for the fine registration, there are used a method for performing coordinate transformation in such a manner that characteristic portions such as pixels values, concentration gradients, edges or the like between images to be registered match with each other, etc.

At step S10, the corresponding sectional image generation unit 8 generates sectional images corresponding to each other at the registered MR image GMR and US image GUS. The sectional position of each of the generated sectional images is designated by the operator.

At step S11, the image output unit 9 displays the generated sectional images on its screen and outputs the same to the outside as image data.

Second Embodiment

An image processing apparatus 1' according to the second embodiment enables image registration even when only one vascular portion branched from a vascular bifurcation point is detected in a vascular tree bone. In the second embodiment, the vascular portion structure detection unit 4 and the matching evaluation unit 5 perform processing different from that in the first embodiment with the image processing apparatus 1 according to the first embodiment as a base.

Figure 10:
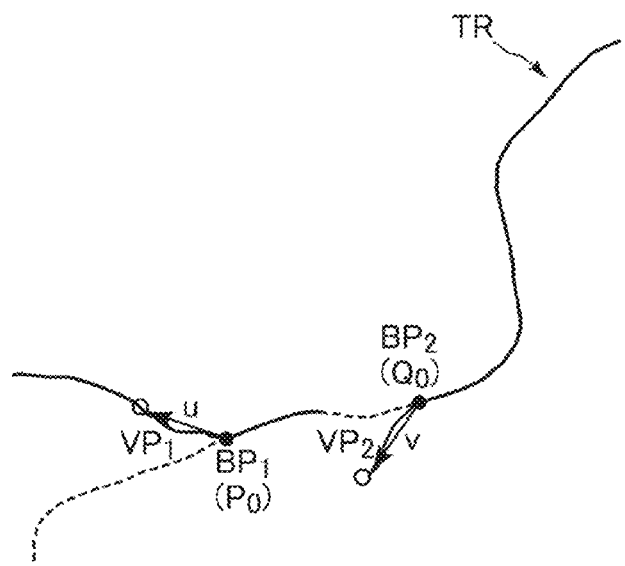
FIG. 10 is a diagram for describing a configuration of an incomplete vascular bifurcation pair in a second embodiment.

The vascular portion structure detection unit 4 detects one or more vascular portion structures at each of an MR vascular tree bone TRMR and a US vascular tree bone TRUS. In the second embodiment, an incomplete vascular bifurcation pair is detected as the vascular portion structures. As shown in FIG. 10, the incomplete vascular bifurcation pair is comprised of a first vascular bifurcation point BP1, a single first vascular portion VP1 extending from the first vascular bifurcation point BP1, a second vascular bifurcation point BP2 close to the first vascular bifurcation point BP1 and different from the first vascular bifurcation point BP1, and a signal second vascular portion VP2 extending from the second vascular bifurcation point BP2 in a vascular tree bone TR. Therefore, the incomplete vascular bifurcation pair is specified and identified by the position of the first vascular bifurcation point BP1, the running direction and length (vector u) of the first vascular portion VP1 extending from the first vascular bifurcation point BP1, the position of the second vascular bifurcation point BP2, and the running direction and length (vector v) of the second vascular portion VP2 extending from the second vascular bifurcation point BP2.

Incidentally, the vascular portion structure detection unit 4 recognizes as a vascular bifurcation point, a position where the direction in which each blood vessel extends changes suddenly, and recognizes vascular portions extending ahead from the position as vascular portions branched from the bifurcation point. Thus, even when only one vascular portion extending from the vascular bifurcation point is detected, the vascular portion structure detection unit 4 can properly detect a vascular bifurcation point and vascular portions extending from the vascular bifurcation point.

The vascular portion structure detection unit 4 specifically performs the following processing.

First, in the same manner as the first embodiment, the vascular portion structure detection unit 4 obtains an MR vascular tree bone TRMR and a US vascular tree bone TRUS from an MR image GMR and a US image GUS. Further, the vascular portion structure detection unit 4 detects two or more vascular bifurcation points at each of the MR vascular tree bone TRMR and the US vascular tree bone TRUS.

Next, the vascular portion structure detection unit 4 determines one vector corresponding to one vascular portion extending from each of an MR vascular bifurcation point BPMR,i and a US vascular bifurcation point BPUS,j with respect to each of the MR vascular bifurcation point BPMR,i and US vascular bifurcation point BPUS,j.

By such processing, at each of the MR vascular tree bone TRMR and the US vascular tree bone TRUS, an incomplete vascular bifurcation pair can be specified by the coordinates of a pixel corresponding to a first vascular bifurcation point, one vector corresponding to one first vascular portion extending from the first vascular bifurcation point, the coordinates of a pixel corresponding to a second vascular bifurcation point, and one vector corresponding to one second vascular portion extending from the second vascular bifurcation point. Incidentally, the incomplete vascular bifurcation pair detected at the MR vascular tree bone TRMR is called an MR incomplete vascular bifurcation pair, and the incomplete vascular bifurcation pair detected at the US vascular tree bone TRUS is called a US incomplete vascular bifurcation pair.

The matching evaluation unit 5 performs a matching evaluation between the incomplete vascular bifurcation pairs for every combination of the MR incomplete vascular bifurcation pair and the US incomplete vascular bifurcation pair. In the second embodiment, the matching evaluation unit 5 registers a smoothing-processed MR vascular image VMR and a smoothing-processed US vascular image VUS with each other in such a manner that the MR incomplete vascular bifurcation pair and US incomplete vascular bifurcation pair targeted for the matching evaluation are overlaid on each other. The matching evaluation unit 5 calculates similarity around the MR incomplete vascular bifurcation pair and US incomplete vascular bifurcation pair targeted for the matching evaluation between the registered MR vascular image VMR and US vascular image VUS. The larger the value of similarity, the more the incomplete vascular bifurcation pairs are evaluated to be more matched. Specifically, the following processing is performed for every combination of the MR incomplete vascular bifurcation pair and US incomplete vascular bifurcation pair targeted for the matching evaluation.

First, the smoothing-processed MR vascular image VMR and US vascular image VUS are placed in a coordinates space common to the MR incomplete vascular bifurcation pair and US incomplete vascular bifurcation pair targeted for the matching evaluation.

This coordinates space is a coordinates space defined in such a manner that a prescribed point of a "first vascular bifurcation point", a "second vascular bifurcation point", or a "middle point of a line segment connecting a straight line extending along a first vascular portion and a straight line extending along a second vascular portion at the shortest distance in the MR incomplete vascular bifurcation pair targeted for the matching evaluation, and the prescribed point in the US incomplete vascular bifurcation pair targeted for the matching evaluation are overlaid on each other, and further a plane including a vector corresponding to the first vascular portion and a vector corresponding to the second vascular portion in the MR incomplete vascular bifurcation pair targeted for the matching evaluation when they are placed in the prescribed point in the MR incomplete vascular bifurcation pair, and a plane including a vector corresponding to a first vascular portion and a vector corresponding to a second vascular portion in the US incomplete vascular bifurcation pair targeted for the matching evaluation when they are placed in the prescribed point in the US incomplete vascular bifurcation pair are superposed on each other. This coordinates space is hereinafter called a second common coordinates space.

In order to place the smoothing-processed MR vascular image VMR in the second common coordinates space, a transformation matrix corresponding to the MR incomplete vascular bifurcation pair targeted for the matching evaluation is determined, and the coordinate transformation of the MR vascular image VMR is performed using the transformation matrix. Likewise, in order to place the smoothing-processed US vascular image VUS in the second common coordinates space, a transformation matrix corresponding to the US incomplete vascular bifurcation pair targeted for the matching evaluation is determined, and the coordinate transformation of the US vascular image VUS is performed using the transformation matrix.

Figures 11A, 11B:
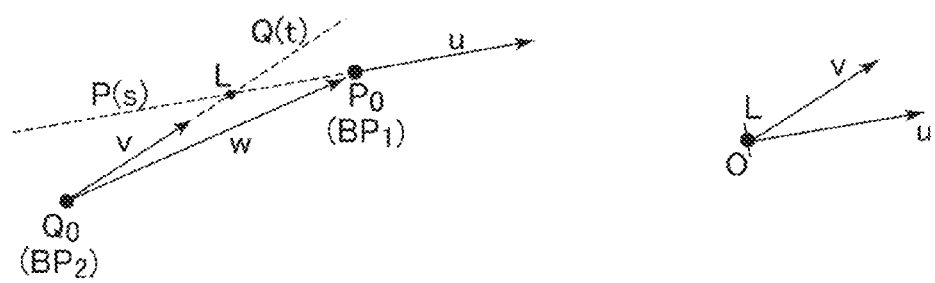
FIGS. 11A and 11B are diagrams for describing vectors that define an incomplete vascular bifurcation pair.

A description will now be made of how to determine the transformation matrix. The transformation matrix is comprised of a point of origin to be taken as the center of the second common coordinates space, and a rotation matrix that defines the posture (orientation) of each incomplete vascular bifurcation pair. As shown in FIG. 11A, a first vascular bifurcation point is taken to be P0=[px, py, pz], and a vector corresponding to a first vascular portion extending from the first vascular bifurcation point P0 is taken to be u=[ux, uy, uz]. Also, a second vascular bifurcation point is taken to be Q0=[qx, qy, qz], and a vector corresponding to a second vascular portion extending from the second vascular bifurcation point Q0 is taken to be v=[vx, vy, vz]. Further, a line segment that connects a straight line extending along the vector u and a straight line extending along the vector v at the shortest distance is assumed to be L. In doing so, the point of origin taken to be the center of the second common coordinates space can be taken as the first vascular bifurcation point P0, the second vascular bifurcation point Q0 or the center O of the shortest distance line segment L as shown in FIG. 11B. Further, the vectors u and v can be moved to and placed in the center or origin of the second common coordinates space. The vectors u and v used herein can be handled in a manner similar to the vectors U and V' corresponding to the two vascular portions in the first embodiment. Thereafter, a transformation matrix for coordinate transformation to the second common coordinates space can be calculated from the incomplete vascular bifurcation pair by using a method similar to that in the first embodiment.

Incidentally, the shortest distance line segment L can be determined in the following manner.

An equation of a three-dimensional linear vector passing through the first vascular bifurcation point P0 and extending along the vector U can be represented as follows:

$$P(s)=P0+s \cdot u$$

where s is a continuously variable parameter value.

Assuming that a linear vector between the first vascular bifurcation point P0 and the second vascular bifurcation point Q0 is w, it is represented as follows:

$$w=P_0-Q_0,$$

Therefore, the following equation is established:

$$P(s)-Q_0=w+s \cdot u$$

Likewise, the following equation is established:

$$Q(t)-P_0=-w+t \cdot v,$$

where t is a continuously variable parameter value.

Combining these two equations yields the following:

$$(P(s)-Q(t))+(P_0-Q_0)=2 \cdot w+s \cdot u-t \cdot v$$

$$(P(s)-Q(t))+w=2 \cdot w+s \cdot u-t \cdot v \qquad \text{Equation (i)}$$

A line segment that connects the linear vector P (s) and the linear vector Q (t) takes the shortest distance when the line segment becomes perpendicular to the linear vector P (s) and the linear vector Q (t). Here, both ends of the line segment that connects the linear vector P (s) and the linear vector Q (t) at the shortest distance are taken to be P (s1) and Q (t1) respectively. Then, since the inner product of the two vectors orthogonal to each other is 0, the following equation is given $$u \cdot (P(s1)-Q(t1))=0$$

Substituting the equation (i) in this equation yields the following:

$$u \cdot (w+s1 \cdot u-t1 \cdot v)=0$$

Accordingly, s1 is represented by the following:

$$s1 = (u \cdot v)[s] \cdot (u \cdot v) + v \cdot w - u \cdot w$$
$$= s1 \cdot (u \cdot v)^2 + (u \cdot v)(v \cdot w) - u \cdot w$$
$$s1 = [(u \cdot v)(v \cdot w) - u \cdot w]/[1 - (u \cdot v)^2]$$

Likewise, t1 is represented by the following:

$$t1=[v \cdot w-(u \cdot v)(u \cdot w)]/[1-(u \cdot v)^2]$$

The shortest distance line segment L is represented by the following equation:

$$L=P(s1)-Q(t1)$$

It can be determined from the vectors u, v and w.

After the smoothing-processed MR vascular image VMR and US vascular image VUS are placed in the second common coordinates space, the matching evaluation unit 5 calculates a mutual correlation coefficient between the MR vascular image VMR and the US vascular image VUS. Specifically, the matching evaluation unit 5 sets an area of a predetermined size including the origin of the second common coordinates space as an evaluation area at each of the MR vascular image VMR and the US vascular image VUS in the second common coordinates space. The evaluation area is taken to be, for example, a three-dimensional area of [64×64×64] pixels centering on its point of origin. Then, the matching evaluation unit 5 calculates similarity, (e.g., a mutual correlation coefficient) in the evaluation area between the MR vascular image VMR and the US vascular image VUS.

Third Embodiment

An image processing apparatus 1″ according to the third embodiment enables image registration even when in a vascular tree bone, no vascular bifurcation point is detected and only vascular portions close to each other are detected. In the third embodiment, the vascular portion structure detection unit 4 and the matching evaluation unit 5 perform processing different from that in the first embodiment with the image processing apparatus 1 according to the first embodiment as a base.

Figure 12:
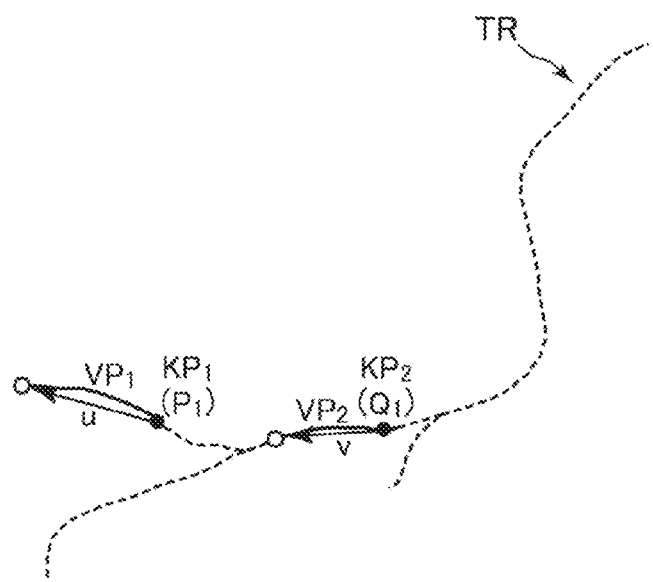
FIG. 12 is a diagram for describing a configuration of a vascular portion pair in a third embodiment.

The vascular portion structure detection unit 4 detects one or more vascular portion structures at each of an MR vascular tree bone TRMR and a US vascular tree bone TRUS. In the third embodiment, a vascular portion pair is detected as the vascular portion structures. As shown in FIG. 12, the vascular portion pair includes a first vascular portion VP1, and a second vascular portion VP2 close to the first vascular portion VP1 and different from the first vascular portion VP1 in a vascular tree bone TR. Therefore, the vascular portion pair is specified and identified by the position of a first vascular portion endpoint KP1, the running direction and length (vector u) of the first vascular portion VP1 extending from the first vascular portion endpoint KP1, the position of a second vascular portion endpoint KP2, and the running direction and length (vector v) of the second vascular portion VP2 extending from the second vascular portion endpoint KP2.

Incidentally, in the vascular tree bone, the vascular portion structure detection unit 4 recognizes each of vascular portions each not including a vascular bifurcation point and recognizes the endpoint of the vascular portion as a vascular portion endpoint.

The vascular portion structure detection unit 4 specifically performs the following processing.

First, in the same manner as the first embodiment, the vascular portion structure detection unit 4 obtains an MR vascular tree bone TRMR and a US vascular tree bone TRUS from an MR image GMR and a US image GUS. Further, the vascular portion structure detection unit 4 detects two or more vascular portion endpoints different from each other at each of the MR vascular tree bone TRMR and the US vascular tree bone TRUS.

Next, the vascular portion structure detection unit 4 determines one vector corresponding to one vascular portion extending from each of an MR vascular portion endpoint KPMR,i and a US vascular portion endpoint KPUS,j with respect to each of them.

By such processing, at each of the MR vascular tree bone TRMR and the US vascular tree bone TRUS, a vascular portion pair can be specified by the coordinates of a pixel corresponding to a first vascular portion endpoint, one vector corresponding to one first vascular portion extending from the first vascular portion endpoint, the coordinates of a pixel corresponding to a second vascular portion endpoint, and one vector corresponding to one second vascular portion extending from the second vascular portion endpoint. Incidentally, the vascular portion pair detected at the MR vascular tree bone TRMR is called an MR vascular portion pair, and the vascular portion pair detected at the US vascular tree bone TRUS is called a US vascular portion pair.

The matching evaluation unit 5 performs a matching evaluation between the vascular portion pairs for every combination of the MR vascular portion pair and the US vascular portion pair. In the third embodiment, the matching evaluation unit 5 registers a smoothing-processed MR vascular image VMR and a smoothing-processed US vascular image VUS with each other in such a manner that the MR vascular portion pair and US vascular portion pair targeted for the matching evaluation are overlaid on each other. The matching evaluation unit 5 calculates similarity around the MR vascular portion pair and US vascular portion pair targeted for the matching evaluation between the registered MR vascular image VMR and US vascular image VUS. The larger the value of similarity, the more the vascular portion pairs are evaluated to be more matched. Specifically, the following processing is performed for every combination of the MR vascular portion pair and US vascular portion pair targeted for the matching evaluation.

First, the smoothing-processed MR vascular image VMR and US vascular image VUS are placed in a coordinates space common to the MR vascular portion pair and US vascular portion pair targeted for the matching evaluation.

This coordinates space is a coordinates space defined in such a manner that a "middle point of a line segment connecting a straight line extending along a first vascular portion and a straight line extending along a second vascular portion at the shortest distance" in an MR vascular portion pair targeted for the matching evaluation, and a "middle point of a line segment connecting a straight line extending along a first vascular portion and a straight line extending a second vascular portion at the shortest distance" in a US vascular portion pair targeted for the matching evaluation are superposed on each other, and further a plane including a vector corresponding to the first vascular portion and a vector corresponding to the second vascular portion in the MR vascular portion pair targeted for the matching evaluation when they are placed in the middle point of the shortest distance line segment in the MR vascular portion pair, and a plane including a vector corresponding to the first vascular portion and a vector corresponding to the second vascular portion in the US vascular portion pair targeted for the matching evaluation when they are placed in the middle point of the shortest distance line segment in the US vascular portion pair are superposed on each other. This coordinates space is hereinafter called a third common coordinates space.

In order to place the smoothing-processed MR vascular image VMR in the third common coordinates space, a transformation matrix corresponding to the MR vascular portion pair targeted for the matching evaluation is determined, and the coordinate transformation of the MR vascular image VMR is performed using the transformation matrix. Likewise, in order to place the smoothing-processed US vascular image VUS in the third common coordinates space, a transformation matrix corresponding to the US vascular portion pair targeted for the matching evaluation is determined, and the coordinate transformation of the US vascular image VUS is performed using the transformation matrix.

Figure 13A:
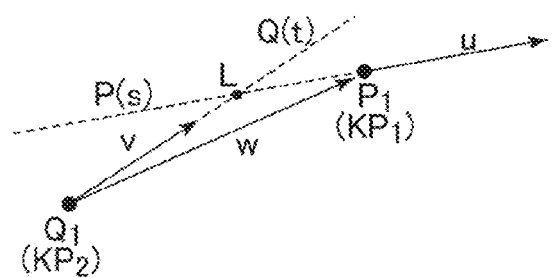
FIGS. 13A and 13B are diagrams for describing vectors that define a vascular portion pair.
Figure 13B:
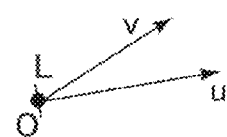

A description will now be made of how to determine the transformation matrix. The transformation matrix is comprised of a point of origin to be taken as the center of the third common coordinates space, and a rotation matrix that defines the posture (orientation) of each vascular portion pair. As shown in FIG. 13A, a first vascular portion endpoint is taken to be P1=[px, py, pz], and a vector corresponding to a first vascular portion extending from the first vascular portion endpoint P1 is taken to be u=[ux, uy, uz]. Also, a second vascular portion endpoint is taken to be Q1=[qx, qy, qz], and a vector corresponding to a second vascular portion extending from the second vascular portion endpoint Q1 is taken to be v=[vx, vy, vz]. Further, a line segment that connects a straight line extending along the vector u and a straight line extending along the vector v at the shortest distance is assumed to be L. In doing so, the point of origin taken to be the center of the third common coordinates space can be taken as the middle point O of the shortest distance line segment L as shown in FIG. 13B. Further, the vectors u and v can be moved to and placed in the center or origin of the third common coordinates space. The vectors u and v used herein can be handled in a manner similar to the vectors U and V' corresponding to the two vascular portions in the first embodiment. Thereafter, a transformation matrix for coordinate transformation to the third common coordinates space can be calculated from the vascular portion pair by using a method similar to that in the first embodiment.

The matching evaluation unit 5 calculates a mutual correlation coefficient between the MR vascular image VMR and the US vascular image VUS after the smoothing-processed MR vascular image VMR and US vascular image VUS are placed in the third common coordinates space. Specifically, in the third common coordinates space, the matching evaluation unit 5 sets an area of a predetermined size including the point of origin of the third common coordinates space as an evaluation area with respect to each of the MR vascular image VMR and the US vascular image VUS. The evaluation area is taken to be, for example, a three-dimensional area of [64×64×64] pixels centering on its point of origin. Then, the matching evaluation unit 5 calculates similarity in the evaluation area between the MR vascular image VMR and the US vascular image VUS (e.g., a mutual correlation coefficient).

Thus, according to the image processing apparatus according to the above embodiments, the coordinate transformation is performed such that some vascular structures are most matched, using the fact that the vascular structures corresponding to each other are substantially the same between the images representing the same subject. Therefore, even when the relevance of the brightness values between the images targeted for registration is low, the registration can be performed without being affected by it. As a result, it is possible to perform higher-accuracy registration.

Incidentally, the image registration methods according to the second and third embodiments may be performed only when the complete vascular bifurcations cannot be detected or may be performed regardless of whether the complete vascular bifurcations can be detected.

Also, in the above embodiments, the matching evaluation is performed on the m vascular portion structures (vascular bifurcation, incomplete vascular bifurcation pair or vascular portion pair) in the MR vascular image, and all combinations with the n vascular portion structures in the US vascular image, but is not limited thereto. For example, the matching evaluation may be performed for every combination of a single vascular portion structure selected by a user out of the n vascular portion structures in the US vascular image, and m vascular structures in the MR vascular image or may be performed for every combination of a single vascular portion structure selected by the user out of the m vascular portion structures in the MR vascular image, and n vascular structures in the US vascular image. The single vascular portion structure selected by the user can be taken as, for example, a vascular portion structure that exists in the vicinity of a region of interest including a tumor or the like in an MR or US image. By doing this, registration with high accuracy in particular can be expected around the region of interest, and hence diagnosis efficiency can be more improved.

The combination of the two images to be registered can be applied not only to the combination of the MR and US images, but also to images of all imaging modalities such as the combinations of CT and US images, and MR and CT images. However, even when the relevance of brightness values is low between two images targeted for registration, the registration method described herein is capable of registration without being almost affected by it. Therefore, the registration method described herein may be particularly effective where a US image having a special drawing form/contrast is contained as an image targeted for registration.

Further, although the above embodiments has shown the example in which the systems and methods described herein are applied to the registration of the images different from each other in imaging modality, the systems and methods described herein can also be applied to the registration of images identical in imaging modality and different in imaging time phase from each other. As such images, there are considered, for example, images before and after surgical operation, images of early and late phases in contrast imaging, etc. Further, the systems and methods described herein can be applied not only to medical images of a human body, but also to animal medical images.

Furthermore, the above embodiments describe an image processing apparatus, but a program for allowing a computer to function as such an image processing apparatus is also one example illustrative of an embodiment of the disclosure.

What is claimed is:

1. An image processing method for performing registration between a first medical image and a second medical image both being three-dimensional images, the image processing method comprising:
    extracting a first vascular image in the first medical image and a second vascular image in the second medical image;
    detecting at least one vascular portion structure including a plurality of vascular portions close or connected to each other with respect to each of the first and second vascular images extracted;
    for each of a plurality of combinations of the at least one vascular portion structure in the first vascular image and the at least one vascular portion structure in the second vascular image, performing coordinate transformation on at least one of the first and second vascular images such that a deviation between the vascular portion structures becomes small, and calculating similarity in a prescribed area including the vascular portion structures between the first and second vascular images; and
    performing coordinate transformation for the registration using the coordinate transformation highest in the calculated similarity.

2. A non-transitory computer-readable medium storing program code configured to cause a computer to perform:
    extracting a first vascular image in a first medical image and a second vascular image in a second medical image;
    detecting at least one vascular portion structure including a plurality of vascular portions close or connected to each other with respect to each of the first and second vascular images extracted by the extraction step;

for each of a plurality of combinations of the at least one vascular portion structure in the first vascular image and the at least one vascular portion structure in the second vascular image, performing coordinate transformation on at least one of the first and second vascular images such that a deviation between the vascular portion structures becomes small, and calculating similarity in a prescribed area including the vascular portion structures between the first and second vascular images; and performing coordinate transformation for registration between the first and second medical images using the coordinate transformation highest in the similarity.

* * * * *